(12) United States Patent
Connor

(10) Patent No.: US 8,105,360 B1
(45) Date of Patent: Jan. 31, 2012

(54) DEVICE FOR DYNAMIC STABILIZATION OF THE SPINE

(75) Inventor: Robert A. Connor, Minneapolis, MN (US)

(73) Assignee: Orthonex LLC, Minneapolis, MN (US)

( * ) Notice: Subject to any disclaimer, the term of this patent is extended or adjusted under 35 U.S.C. 154(b) by 292 days.

(21) Appl. No.: 12/460,261

(22) Filed: Jul. 16, 2009

(51) Int. Cl.
*A61B 17/70* (2006.01)

(52) U.S. Cl. ........................................ 606/257; 606/246

(58) Field of Classification Search .................. 606/246, 606/253–263
See application file for complete search history.

(56) References Cited

U.S. PATENT DOCUMENTS

| | | | |
|---|---|---|---|
| 4,932,975 A | 6/1990 | Main et al. |
| 5,092,866 A | 3/1992 | Breard et al. |
| 5,375,823 A | 12/1994 | Navas |
| 5,480,401 A | 1/1996 | Navas |
| 5,540,688 A | 7/1996 | Navas |
| 6,290,700 B1 | 9/2001 | Schmotzer |
| 6,296,643 B1 | 10/2001 | Hopf et al. |
| 6,299,613 B1 | 10/2001 | Ogilvie et al. |
| 6,475,220 B1 | 11/2002 | Whiteside |
| 6,616,669 B2 | 9/2003 | Ogilvie et al. |
| 6,835,207 B2 | 12/2004 | Zacouto et al. |
| 6,986,771 B2 | 1/2006 | Paul et al. |
| 6,989,011 B2 | 1/2006 | Paul et al. |
| 7,083,621 B2 | 8/2006 | Shaolian et al. |
| 7,125,410 B2 | 10/2006 | Freudiger |
| 7,229,441 B2 | 6/2007 | Trieu et al. |
| 7,326,210 B2 | 2/2008 | Jahng et al. |
| 7,329,258 B2 | 2/2008 | Studer |
| 7,361,196 B2 | 4/2008 | Fallin et al. |
| 7,604,653 B2 * | 10/2009 | Kitchen .................. 606/257 |
| 2004/0049190 A1 | 3/2004 | Biedermann et al. |
| 2004/0143264 A1 | 7/2004 | McAfee |
| 2004/0152972 A1 | 8/2004 | Hunter |
| 2004/0167520 A1 | 8/2004 | Zucherman et al. |
| 2004/0215191 A1 | 10/2004 | Kitchen |
| 2005/0065516 A1 | 3/2005 | Jahng |
| 2005/0085814 A1 | 4/2005 | Sherman |
| 2005/0124991 A1 | 6/2005 | Jahng |
| 2005/0149020 A1 | 7/2005 | Jahng |
| 2005/0154390 A1 | 7/2005 | Biedermann et al. |
| 2005/0171543 A1 | 8/2005 | Timm et al. |
| 2005/0177156 A1 | 8/2005 | Timm et al. |
| 2005/0203514 A1 * | 9/2005 | Jahng et al. ............... 606/61 |
| 2005/0245929 A1 | 11/2005 | Winslow et al. |
| 2005/0288672 A1 | 12/2005 | Ferree |
| 2006/0004447 A1 | 1/2006 | Mastrorio et al. |
| 2006/0036256 A1 | 2/2006 | Carl et al. |
| 2006/0036259 A1 | 2/2006 | Carl et al. |
| 2006/0036324 A1 | 2/2006 | Sachs et al. |

(Continued)

OTHER PUBLICATIONS

U.S. Appl. No. 12/322,837, filed Feb. 7, 2009, Connor, Robert.

*Primary Examiner* — Eduardo C Robert
*Assistant Examiner* — Stuart S Bray

(57) ABSTRACT

This invention is an implantable device for dynamic stabilization of the spine that allows desirable spinal movement and prevents undesirable spinal movement. The device comprises: a longitudinal sequence of incompressible segments; a plurality of substantially-inelastic members that connect the segments through non-central channels; and a plurality of motion-dampening members. Desirable movement includes naturally-dampened flexion, extension, lateral bending, and torsion of the spine within a normal range of motion. Desirable movement may also include gradual correction of abnormal spinal curvature. Preventing undesirable movement includes preventing movement of the spine outside its normal range of motion. Preventing undesirable movement may also include alleviating intervertebral disc compression by providing vertebral support.

18 Claims, 7 Drawing Sheets

U.S. PATENT DOCUMENTS

| | | |
|---|---|---|
| 2006/0047282 A1 | 3/2006 | Gordon |
| 2006/0084983 A1 | 4/2006 | Kim |
| 2006/0084985 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085073 A1 | 4/2006 | Raiszadeh |
| 2006/0085074 A1 | 4/2006 | Raiszadeh |
| 2006/0129147 A1 | 6/2006 | Biedermann et al. |
| 2006/0212033 A1 | 9/2006 | Rothman et al. |
| 2006/0247637 A1 | 11/2006 | Colleran et al. |
| 2006/0265077 A1 | 11/2006 | Zwirkoski |
| 2007/0016193 A1 | 1/2007 | Ritland |
| 2007/0123871 A1 | 5/2007 | Jahng |
| 2007/0161991 A1 | 7/2007 | Altarac et al. |
| 2007/0173832 A1 | 7/2007 | Tebbe et al. |
| 2007/0173855 A1 | 7/2007 | Winn et al. |
| 2007/0198088 A1 | 8/2007 | Biedermann et al. |
| 2007/0233075 A1 | 10/2007 | Dawson |
| 2007/0233098 A1 | 10/2007 | Mastrorio et al. |
| 2007/0270821 A1 | 11/2007 | Trieu et al. |
| 2007/0270860 A1 | 11/2007 | Jackson |
| 2007/0282443 A1 | 12/2007 | Globerman et al. |
| 2007/0288011 A1 | 12/2007 | Logan |
| 2007/0293862 A1 | 12/2007 | Jackson |
| 2008/0021466 A1 | 1/2008 | Shadduck et al. |
| 2008/0045951 A1 | 2/2008 | Fanger et al. |
| 2008/0097441 A1 | 4/2008 | Hayes et al. |
| 2008/0114357 A1 | 5/2008 | Allard et al. |
| 2008/0125777 A1 | 5/2008 | Veldman et al. |
| 2008/0154307 A1 | 6/2008 | Colleran et al. |
| 2008/0177317 A1 | 7/2008 | Jackson |
| 2008/0177388 A1 | 7/2008 | Patterson et al. |
| 2008/0221620 A1 | 9/2008 | Krause |
| 2008/0269904 A1 | 10/2008 | Voorhies |
| 2008/0288073 A1 | 11/2008 | Renganath et al. |
| 2008/0312693 A1 | 12/2008 | Trautwein et al. |
| 2008/0319486 A1 | 12/2008 | Hestad et al. |
| 2009/0012562 A1 | 1/2009 | Hestad et al. |
| 2009/0048631 A1* | 2/2009 | Bhatnagar et al. ............ 606/246 |
| 2009/0287251 A1* | 11/2009 | Bae et al. ...................... 606/254 |
| 2010/0069962 A1* | 3/2010 | Harms et al. .................. 606/254 |
| 2010/0211104 A1* | 8/2010 | Moumene et al. ............. 606/257 |
| 2011/0046676 A1* | 2/2011 | Droulout et al. .............. 606/257 |

* cited by examiner

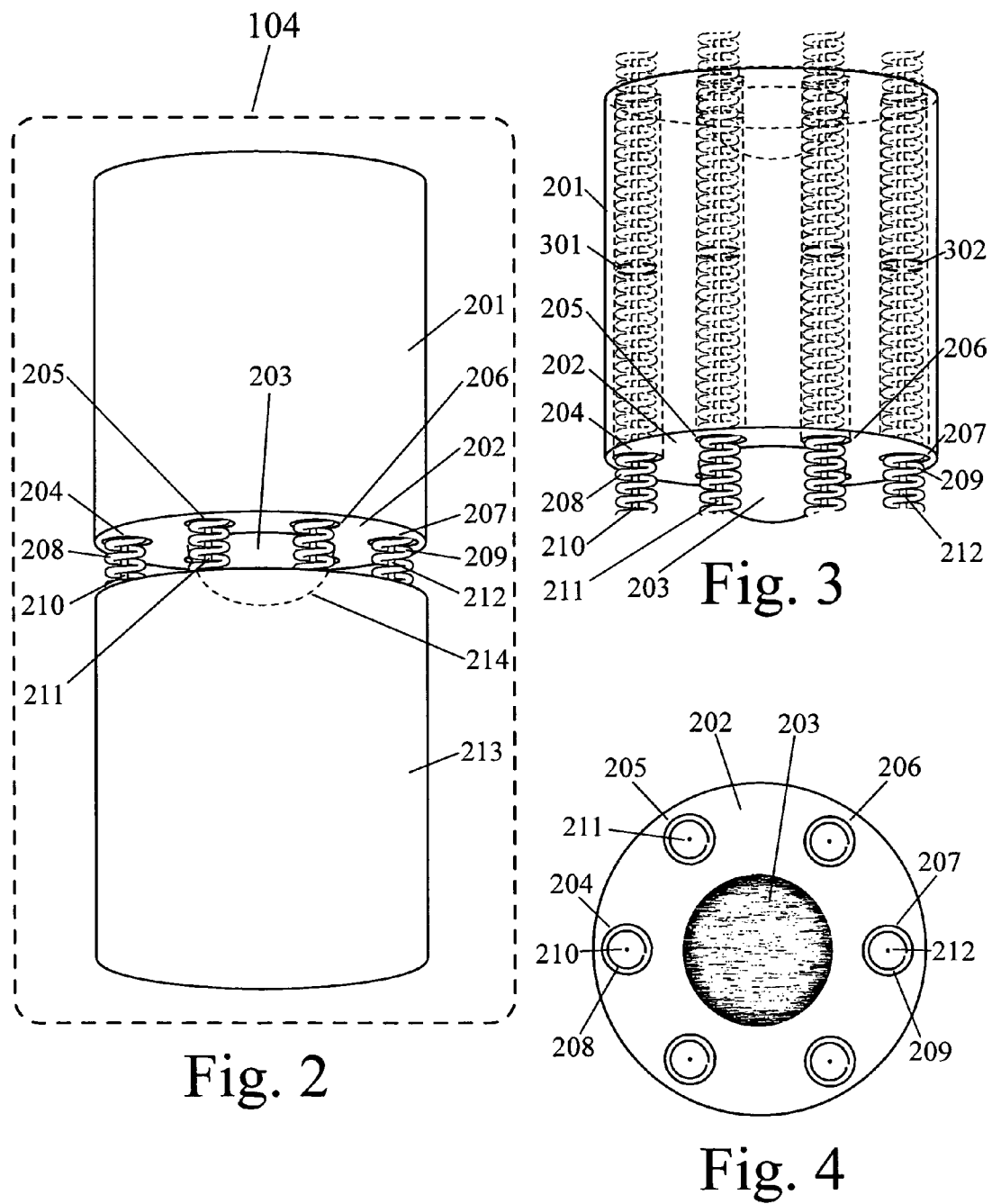

DEVICE FOR DYNAMIC STABILIZATION OF THE SPINE

CROSS-REFERENCE TO RELATED APPLICATIONS

This patent application claims the priority benefit of U.S. patent application Ser. No. 12/322,837 entitled "Dynamic stabilization device with tilting rigid segments and non-central tensile members" filed on Feb. 7, 2009 by Robert A. Connor.

FEDERALLY SPONSORED RESEARCH

Not Applicable

SEQUENCE LISTING OR PROGRAM

Not Applicable

BACKGROUND

1. Field of Invention

This invention relates to implants for dynamic stabilization of the spine.

2. Related Art

Chronic lower back pain is a very common, significant, and costly health problem in the United States and the entire world. It is estimated that more than ten million people in the U.S. suffer from chronic back pain at any a given time, the annual prevalence of lower back pain is in the range of 15-45% of the population, and thoracic and lumbar spinal disorders affect nearly three-quarters of the U.S. population some time during their lives. Chronic back pain can be debilitating, interfering with one's ability to work and enjoy recreational activities. It is the most common activity-limiting condition affecting people under the age of 45.

The leading cause of chronic lower back pain is the degeneration of the semi-flexible discs between spinal vertebrae. There are non-invasive approaches to address chronic back pain, but sometimes they are inadequate and more invasive methods are required. Historically, a common invasive method has been to fuse selected spinal vertebrae together in an effort to eliminate disc movement and stop the pain. More than 150,000 lumbar fusions are done each year to immobilize selected vertebrae.

However, there are problems associated with fusing vertebrae. Fusion-related problems include: undesirable restriction of natural spine movement (flexion, extension, lateral bending, and torsion) in fused segments; greater stress and degeneration affecting spinal segments adjacent to fused segments (a phenomenon called "transition syndrome"); bone loss in the immobilized segments; failure to stop the pain in approximately 20-25% of fusion cases; irreversibility of the procedure; and the invasiveness, health risks, and relatively long recovery period associated with the surgery.

Due to these problems associated with the complete immobilization of selected vertebrae in fusion, there has been an increasing trend toward alternative methods of addressing back pain that preserve some spinal mobility. "Dynamic stabilization" is the term for methods that seek to maintain desirable spinal movement, but limit undesirable spinal movement. The ultimate form of dynamic stabilization would be to artificially recreate the natural biodynamics of a healthy spine. Since the original spine is not entirely replaced, the challenge is to recreate natural biodynamics in an integrated manner with those portions of the original spine which are working properly and remain in place. Due to the complexity of spinal biomechanics, this is not an easy goal.

With respect to limiting undesirable movement, dynamic stabilization seeks to: relieve the load and correct improper vertebral movement in areas where pain is caused by compression and improper vertebral movement; maintain proper rigidity, stabilization, and vertical support of the spinal column; avoid abnormal range of motion; and ensure the long-term durability of the spinal structure, including any implants.

With respect to allowing or enhancing desirable movement, dynamic stabilization seeks to allow normal biomechanical direction and range of motion including flexion (bending forward/anteriorly), extension (bending backward/posteriorly), lateral bending (right and left side bending), torsion (axial rotational movement), and limited longitudinal elongation or compression (so-called "shock absorber" functionality). In addition to the mobility and comfort advantages for patients, allowing normal motion can also help avoid loss of bone density for diseased segments and more evenly distribute load across different portions of the spinal column to avoid creating stress-induced problems elsewhere. Allowing desirable spinal movement is particularly important for young patients.

Dynamic stabilization can be implemented in the intervertebral space (such as with artificial discs), in the space posterior to the vertebrae (such as with flexible connecting rods), or in both places simultaneously. With respect to the intervertebral space, malfunctioning disc tissue may be replaced with an artificial alternative. With respect to the space posterior to vertebrae, selected vertebrae may be connected by an elastic cord, a cord with spacer, a flexible rod, or by some other type of connecting member that allows some movement. Both spaces may be addressed in combination to distribute loading in a manner that approximates the loading distribution in a healthy spine. This invention focuses on dynamic stabilization outside the intervertebral space. This invention may be used in combination with devices in the intervertebral space, such as artificial discs, but the opportunities and challenges for connectors outside this space are sufficiently different to merit focused review.

Considerable progress has been made toward methods of dynamic stabilization to provide the correct balance of allowing desirable movement and limiting undesirable movement. However, this remains a challenge. All current treatment options have limitations. There is still a need for a new approach to dynamic stabilization that addresses these limitations and provides better treatment options for the millions of people who suffer from chronic back pain.

Problems with current options can be grouped into three general categories: problems from reduced desired movement; problems from allowed undesirable movement; and other types of problems. In this section, I now list these problems grouped by category. Then, I review the main methods for dynamic stabilization outside the intervertebral space and discuss the potential problems with each method. This sets the stage for the present invention for dynamic stabilization disclosed herein that corrects many of these problems.

The array of potential problems associated with too little movement after implantation includes the following. The method may undesirably restrict natural spine movement in one or more directions (flexion, extension, lateral bending, and torsion). The method may immobilize a section of the spine causing greater stress, unnatural movement, and degeneration of adjacent portions of the spine (a phenomenon called "transition syndrome"). The method may not be adjustable to meet the specific needs and features of different patients. The method may not be adjustable after implantation to refine therapy or accommodate patient growth.

The array of potential problems associated with too much movement after implantation includes the following. The method may allow multi-directional movement without the ability to selectively control the degree or range of movement in different directions (flexion, extension, lateral bending, and torsion). The method may not provide sufficient vertical support of the spinal column. The method may be prone to mechanical or material failure due to repeated flexing of materials or components. The method may involve implants that are subject to slipping, shifting, or extrusion. The method may cause scarring, pinching, or other damage to nearby soft tissue.

Other potential problems include the following. The method may involve implantation of a relatively-large structure and a relatively-invasive surgical procedure. The method may require a complex and time-consuming surgical procedure. The method may require an expensive array of parts in different sizes. The method may be difficult or impossible to reverse due to invasion and destruction of body tissue. The method may not stop the pain, as is the case in approximately 20-25% of fusion operations.

Let us now consider the main methods in the related art for dynamic stabilization with intervertebral connectors outside the intervertebral space and discuss the problems of each method:

1. Flexible Elastic Members Only

This method uses only flexible elastic members (such as elastic tethers, bands, cords, or cables) to connect vertebrae outside the intervertebral space. An early example of this method is the Graf ligament. The Graf ligament consists of securing elastic bands to spinous processes and/or pedicle screws. It provides some stabilization while also allowing some flexion and torsion movement. Related art that appears to use this approach includes: U.S. Pat. Nos. 5,092,866 (Breard et al.), 7,125,410 (Freudiger), 7,229,441 (Trieu et al.) and U.S. Patent Application 20080269904 (Voorhies, R).

Potential problems with this method include: inconsistency of motion control can occur when elasticity changes over time with repeated motion and material stress; it may limit the patient's ability for forward flexion; it may not sufficiently offload stress from a compressed disc or provide sufficient vertical support of the spinal column; it is difficult to adjust (non-invasively) after implantation in order to refine therapy or accommodate patient growth; it can allow multi-directional movement without the ability to selectively control the degree or range of movement in different directions; and it can involve a relatively time-consuming surgical procedure.

2. Flexible Inelastic Members Only

This method uses flexible, but relatively inelastic, members (such as flexible rods, wires, inelastic fibers, or cables) to connect vertebrae outside the intervertebral space. Related art that appears to use this approach includes: U.S. Pat. No. 6,475,220 (Whiteside) and U.S. Patent Application 20060047282 (Gordon, Jeffrey). Potential problems with this method include: inconsistent motion control or breakage due to repeated flexing and material stress over time; the inelastic members may restrict flexion, extension, lateral bending, and torsion; it may immobilize a section of the spine which causes greater stress, unnatural movement, and degeneration of adjacent portions of the spine ("transition syndrome"); it may provide insufficient vertical support of the spinal column; it may not be adjustable after implantation to refine therapy or accommodate patient growth; it may allow multi-directional movement without the ability to selectively control the degree or range of movement in different directions (flexion, extension, lateral bending, and torsion); and it may cause scarring, pinching, or other damage to nearby soft tissue.

3. Springs or Spring-Like Cut-Metal Members Only

This method uses springs or spring-like metal members with (helical) cuts to connect vertebrae outside the intervertebral space. Related art that appears to use this approach includes: U.S. Pat. Nos. 6,986,771 (Paul et al.), 6,989,011 (Paul et al.), 7,326,210 (Jahng et al.), 7,329,258 (Studer) and U.S. Patent Applications 20050065516 (Jahng, Tae-Ahn), 20050085814 (Sherman, Michael), 20050124991 (Jahng, Tae-ahn), 20050149020 (Jahng, Tae-Ahn), 20050154390 (Biedermann et al.), 20050203514 (Jahng et al.), 20050288672 (Ferree, Bret A.), 20060129147 (Biedermann et al.), 20060212033 (Rothman et al.), 20060247637 (Colleran et al.), 20070016193 (Ritl, Stephen), 20070123871 (Jahng, Tae-Ahn), 20070198088 (Biedermann et al.), 20070270860 (Jackson, Roger), 20070282443 (Globerman et al.), 20080021466 (Shadduck et al.), 20080045951 (Fanger et al.), 20080154307 (Colleran et al.), 20080177317 (Jackson, Roger), 20080221620 (Krause, William), 20080269904 (Voorhies, R), and 20080312693 (Trautwein et al.).

Potential problems with this method include: inconsistency of motion control or mechanical failure due to repeated flexing of metal components; it may cause multi-directional movement without the ability to selectively control the degree or range of movement in different directions; it may not provide sufficient vertical support of the spinal column; it may not be adjustable before implantation to meet the specific needs and features of different patients; it may not be adjustable after implantation to refine therapy or accommodate patient growth; and it may cause scarring, pinching, or other damage to nearby soft tissue.

4. Flexible Member with Flexible Inelastic Members Inside

This method uses a flexible member (such as a flexible cylinder or spring) that contains flexible, but inelastic members inside (such as inelastic wires, fibers, or cables) to connect vertebrae outside the intervertebral space. Related art that appears to use this approach includes U.S. Patent Application 20070270821 (Trieu et al.). Potential problems with this method include: it may be prone to material failure due to repeated flexing of materials or components; the inelastic members may undesirably restrict natural spine movement in one or more directions (flexion, extension, lateral bending, and torsion); it may not provide sufficient vertical support of the spinal column; it may not be adjustable after implantation to refine therapy or accommodate patient growth; and it may cause multi-directional movement without the ability to selectively control the degree or range of movement in different directions (flexion, extension, lateral bending, and torsion).

5. Flexible Member with Rigid Rod(s) Inside

This method uses a flexible member (such as a flexible cylinder or spring) that contains one or more rigid rod-like members to connect vertebrae outside the intervertebral space. For example, the device may be a flexible tube with multiple channels into which may be inserted rods with different shapes or degrees of flexibility, thereby customizing the shape and flexibility of the device. Related art that appears to use this approach includes: U.S. Patent Applications 20040049190 (Biedermann et al.), 20040143264 (McAfee, Paul), 20040215191 (Kitchen, Michael), 20080125777 (Veldman et al.), 20080319486 (Hestad et al.), and 20090012562 (Hestad et al.).

Potential problems with this method include: it may be prone to mechanical or material failure due to repeated flexing of materials or components (especially if the inner rigid members are thin); it may require an expensive array of parts (such as multiple size and shape rigid inserts); it may undesirably restrict natural spine movement in one or more directions (flexion, extension, lateral bending, and torsion); it may cause immobility of a section of the spine which causes greater stress, unnatural movement, and degeneration of adjacent portions of the spine ("transition syndrome"); and it may not be adjustable after implantation to refine therapy or accommodate patient growth.

6. Non-Contiguous Rigid Segments Connected by Flexible Member(s)

This method uses non-contiguous rigid segments (such as plastic/metal cylinders/ovals) whose only connection is one or more flexible members (such as wires, cords, or cables) in order to connect vertebrae outside the intervertebral space. Related art that appears to use this approach includes: U.S. Pat. Nos. 6,296,643 (Hopf et al.), 6,299,613 (Ogilvie et al.), 6,616,669 (Ogilvie et al.), 7,083,621 (Shaolian et al.), and 7,326,210 (Jahng et al.) and U.S. Patent Applications 20040167520 (Zucherman et al.), 20050065516 (Jahng, Tae-Ahn), 20050124991 (Jahng, Tae-ahn), 20050149020 (Jahng, Tae-Ahn), 20050203514 (Jahng et al.), 20050245929 (Winslow et al.), 20060265077 (Zwirkoski, Paul), 20070123871 (Jahng, Tae-Ahn), 20070233075 (Dawson, John), and 20080114357 (Allard et al.).

Potential problems with this method include: lack of solid or multiple-tensile connections between the rigid segments makes it very difficult to control the amount of flexion, lateral bending, or longitudinal support; it may be prone to mechanical or material failure due to repeated flexing, especially at the junctions between rigid and flexible members; it may not be adjustable to meet the specific needs and features of different patients; it may not be adjustable after implantation to refine therapy or accommodate patient growth; it may involve implants that are subject to slipping, shifting, or extrusion; and it may cause scarring, pinching, or other damage to nearby soft tissue.

7. Contiguous Rigid Segments Connected by a Central Flexible Member

This method uses contiguous rigid segments (such as plastic or metal cylinders) that are connected through their centers by a flexible member (such as a wire, cord, or cable) to connect vertebrae outside the intervertebral space. Related art that appears to use this approach includes: U.S. Pat. Nos. 6,290,700 (Schmotzer), 7,083,621 (Shaolian et al.), and 7,326,210 (Jahng et al.) and U.S. Patent Applications 20050065516 (Jahng, Tae-Ahn), 20050124991 (Jahng, Tae-ahn), 20050149020 (Jahng, Tae-Ahn), 20050203514 (Jahng et al.), 20060265077 (Zwirkoski, Paul), 20070123871 (Jahng, Tae-Ahn), 20070288011 (Logan, Joseph), and 20080269904 (Voorhies, R).

Potential problems with this method include: the central location of the connecting flexible member provides poor leverage and control over flexion and lateral bending; also, due to the central location of the connecting flexible member, changes in tension of the connecting member do not control the direction of curvature of the multi-segment structure; also due to the central location of the connecting flexible member, it is difficult to have rounded contiguous connections such as a ball-and-socket joint that would otherwise help to avoid mechanical failure; and it may cause scarring, pinching, or other damage to nearby soft tissue.

8. Contiguous Rigid Segments Connected by One Type of Non-Central Member

This method uses contiguous rigid segments (such as plastic or metal cylinders) that are connected outside their centers by one type of flexible member (such as wires, cords, or cables) to connect vertebrae outside the intervertebral space. This method is quite new. The only related art that appears to use this approach is unpublished U.S. patent application Ser. No. 12/322,837 (Connor, Robert).

9. Telescoping Rigid Members with Springs

This method features telescoping rigid components (such as telescoping concentric hollow cylinders) with springs or other flexible members, inside or outside those telescoping components, to connect vertebrae outside the intervertebral space. Related art that appears to use this approach includes: U.S. Pat. Nos. 5,480,401 (Navas), 5,540,688 (Navas), 7,361,196 (Fallin et al.) and U.S. Patent Applications 20050171543 (Timm et al.), 20050177156 (Timm et al.), 20050288672 (Ferree, Bret), 20060036256 (Carl et al.), 20060036259 (Carl et al.), 20060036324 (Sachs et al.), 20060084983 (Kim, Daniel), 20060084985 (Kim, Daniel), 20060084988 (Kim, Daniel), 20060085069 (Kim, Daniel), 20060085070 (Kim, Daniel), 20060247637 (Colleran et al.), 20070161991 (Altarac et al.), 20070173832 (Tebbe et al.), 20080097441 (Hayes et al.), 20080154307 (Colleran et al.), and 20080177317 (Jackson, Roger).

Potential problems with this method include: when the telescoping members are directly connected to vertebrae and are largely-parallel to the longitudinal axis of the spine, then these members can restrict natural flexion and lateral bending movement of the spine; it may be prone to mechanical or material failure due to repeated flexing of materials or components; it may be difficult to adjust to customize the device for different patients; it may be difficult to adjust over time to refine treatment or respond to patient growth; when there are multiple telescoping members (such as several for each intervertebral span) that are each individually connected to the vertebrae using screws, then these multiple intrusions can further stress the structural integrity of vertebrae that are already weakened by injury or disease; and it may cause scarring, pinching, or other damage to nearby soft tissue.

10. Telescoping Rigid Members with a Flowable Substance Inside

This method features hydraulic or pneumatic telescoping members (such as concentric hollow cylinders) with a flowable substance (such as a liquid or a gas) inside to connect vertebrae, including some applications for artificial discs inside the intervertebral space. Related art that appears to use this approach includes: U.S. Pat. Nos. 4,932,975 (Main et al.), 5,375,823 (Navas), and 6,835,207 (Zacouto et al.) and U.S. Patent Applications 20040152972 (Hunter, Mark), 20060085073 (Raiszadeh, Kamshad), 20060085074 (Raiszadeh, Kamshad), 20070173855 (Winn et al.), and 20080288073 (Renganath et al.).

Most of the related art with respect to telescoping members involves artificial discs in the intervertebral space. Intervention in the intervertebral space is often insufficient; stabilization is often required outside (alone or in combination) the intervertebral space. The latter is the focus of this present invention.

With respect to stabilization outside the intervertebral space using telescoping members, the related art appears to involve direct attachment of telescoping members to the vertebrae. Further, most of the current or proposed applications in the related art appear to involve one or two relatively-large telescoping members per vertebral space spanned.

There are problems with these applications of telescoping members in the related art. First, directly attaching one or two telescoping members to the vertebrae restricts natural flexion and bending, especially if the telescoping members are parallel to the longitudinal axis of the spine. The telescoping action of concentric cylinders only occurs in a straight line; it allows straight-line contraction or extension, but not flexion or bending. Second, if you use a large number of telescoping members (ten, for example) to create an angled configuration that allows flexion and bending, but you connect each member directly to the bone (creating ten holes for ten screws, for example), then you can weaken vertebrae that are already weakened by injury or disease. Third, multiple telescoping members that are individually attached to the vertebrae form an irregularly-shaped moving structure that is difficult to isolate from body tissue and fluids with a protective barrier.

11. Telescoping Rigid Members with Gears or Other Components

This method features telescoping rigid components (such as concentric hollow cylinders) moved by gears or other methods that are neither springs nor flowable substances to connect vertebrae outside the intervertebral space. Related art that appears to use this approach includes: U.S. Patent Applications 20060004447 (Mastrorio et al.), 20060247637 (Colleran et al.), 20070233098 (Mastrorio et al.), 20070282443 (Globerman et al.), 20070288011 (Logan, Joseph), 20080045951 (Fanger et al.), and 20080269904 (Voorhies, R).

In addition to the problems associated with telescoping rigid members filled with a flowable substance discussed above, rigid members with gears or other methods may be prone to mechanical failure due to repeated movement of materials or components.

12. Integrated Configurations of Differentially-Flexible Materials

This method features (generally-solid) structures with integrated configurations of differentially-flexible materials to connect vertebrae outside the intervertebral space. For example, they may be a relatively-solid composite rod with a rigid core and flexible outer layer, or vice versa. Related art that appears to use this approach includes: U.S. Pat. No. 7,326,210 (Jahng et al.) and U.S. Patent Applications 20050065516 (Jahng, Tae-Ahn), 20050149020 (Jahng, Tae-Ahn), 20070293862 (Jackson, Roger), 20080177317 (Jackson, Roger), 20080177388 (Patterson et al.), 20080319486 (Hestad et al.), and 20090012562 (Hestad et al.).

This broadly-defined method can have a very wide range of possible designs, so it is difficult to pin down specific advantages and problems. Due to this design flexibility, this method has considerable upside potential, but is also vulnerable to almost all of the potential problems that listed above. It may be particularly vulnerable to mechanical or material failure due to shearing of the differentially-flexible materials within a solid member with repeated movement over time. It may also undesirably restrict natural spine movement if the rigid material is dominant or fail to offer sufficient motion control if the flexible material is dominant. It also may be difficult to adjust after implantation to refine therapy or accommodate patient growth.

GOAL AND SUMMARY OF THIS INVENTION

The goal of the invention disclosed herein is to allow desirable movement of the spine while preventing undesirable movement of the spine. This is called "dynamic stabilization." Desirable movement includes naturally-dampened flexion, extension, lateral bending, and torsion of the spine within a normal range of motion. Desirable movement may also include gradual correction of abnormal spinal curvature. Preventing undesirable movement includes preventing movement of the spine outside its normal range of motion. Preventing undesirable movement may also include alleviating intervertebral disc compression by providing vertebral support.

This invention is a longitudinal implantable device for dynamic stabilization of the spine comprising: (1) a longitudinal sequence of incompressible segments that connect spinal vertebrae, contain non-central longitudinal channels, and provide spinal support; (2) substantially-inelastic members (such as wires) that run through these non-central channels, connect the incompressible segments, and restrict spinal movement so that it remains within a desirable range of motion; and (3) motion-dampening members (such as springs) that also run through the non-central channels and advantageously-dampen spinal movement within the desirable range of motion. This novel invention addresses many of the problems of the dynamic stabilization methods in the related art that were discussed above.

In contrast to methods in the related art using flexible elastic members only or flexible inelastic members only, this present invention provides good support for the spinal column, provides selective control of the degree and range of movement in different directions, and has potential for adjustment after implantation.

In contrast to methods in the related art using springs or spring-like cut-metal members only, this present invention provides good support for the spinal column, provides selective control of the degree or range of movement in different directions, has potential for adjustment after implantation, and has no flexing metal springs or spring-like structures that may weaken and break with repeated movement.

In contrast to methods in the related art using flexible members with flexible inelastic members inside or flexible members inside, this present invention provides good vertical support for the spinal column, provides selective control of the degree or range of movement in different directions, and has potential for adjustment after implantation.

In contrast to methods in the related art using flexible members with rigid rods inside, this present invention does not have flexing (thin) rods that may weaken or break with repeated movement, does not require an expensive array of parts such as multiple size and shape rigid inserts, allows natural spine movement in multiple directions (flexion, extension, lateral bending, and torsion), and has potential for non-invasive adjustment after implantation.

In contrast to methods in the related art using non-contiguous rigid segments connected by flexible members, this present invention: provides good vertical support for the spinal column, provides selective control of the degree or range of movement in different directions; and has potential for non-invasive adjustment after implantation.

In contrast to methods in the related art using contiguous rigid segments connected by a central flexible member, this present invention provides good leverage for selective control of the degree or range of movement in different directions, allows the use rounded of rounded (e.g. ball-and-socket) joints between rigid segments because there is no connecting flexible member in the segment center; and has potential for non-invasive adjustment after implantation.

In contrast to methods in the related art using contiguous rigid segments connected by only one type of non-central flexible member, the use of both inelastic and motion-dampening longitudinal members (such as wires and springs) allows: firmer restriction of movement outside the desired range of motion; and more precise control of motion-dampening within the desired range of motion.

In contrast to methods in the related art using telescoping members with springs or gears, this present invention allows natural flexion and lateral bending movement of the spine, is less prone to mechanical or material failure, and has the potential for non-invasive adjustment after implantation.

In contrast to methods in the related art using telescoping members with a flowable substance inside that are directly attached to the vertebrae, this present invention provides selective control of the degree or range of movement in different directions without weakening the vertebrae with a large number of holes, and avoids having an irregularly-shaped moving structure which is difficult to isolate from surrounding body tissue and liquids.

In contrast to methods in the related art using integrated configurations of differentially-flexible materials, this present invention provides good vertical support for the spinal column, is less prone to mechanical or material failure because there are no shearing or large-scale flexing members, provides selective control of the degree or range of movement in different directions, and has the potential for non-invasive adjustment after implantation to refine therapy or accommodate patient growth.

To summarize, this invention is novel and has many advantages over current methods of dynamic stabilization outside the intervertebral space. It has considerable potential to restore normal spinal biomechanics and offers new possibilities for adjustment before and after implantation. It can be a useful addition to the treatment options available for the millions of people suffering from chronic lower back pain.

INTRODUCTION TO THE FIGURES

These figures show different examples of how this invention may be embodied. However, these examples are not exhaustive. These figures do not limit the full generalizability of the claims.

FIG. 2 shows details for one rod-like embodiment of this device. It shows a primarily-opaque side view of two of the multiple segments that comprise the rod-like embodiment that connects vertebrae.

FIG. 3 shows a partially-transparent side view of the upper cylindrical segment. The segment has six non-central longitudinal channels. Each channel contains a longitudinal spring with a longitudinal wire running through its center.

FIG. 4 shows an opaque view of the bottom end of the upper cylindrical segment in FIG. 2.

Figures 5, 6, 7:
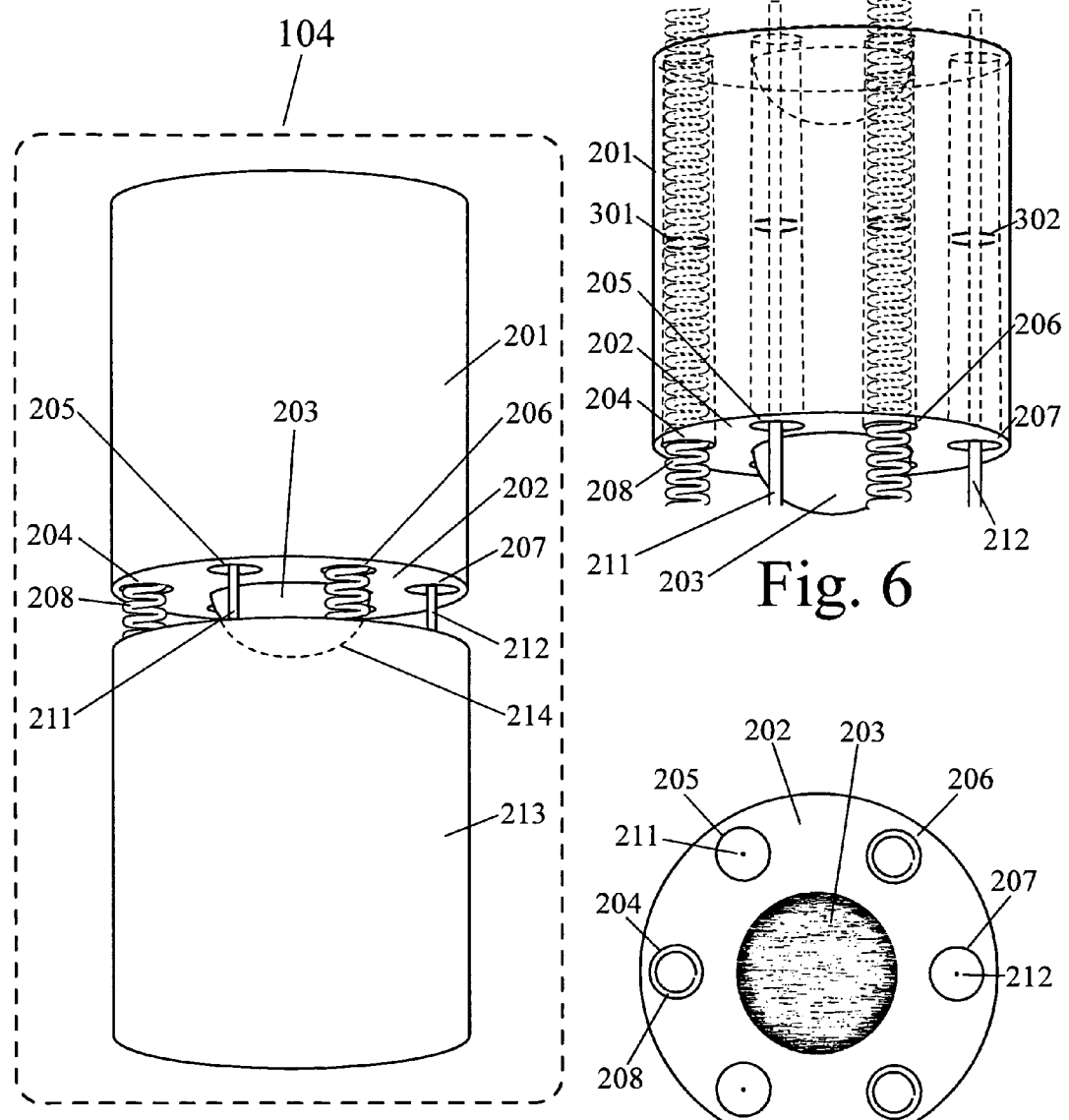

FIG. 5 shows details for a second rod-like embodiment of this device. It shows a primarily-opaque side view of two of the multiple segments that comprise the rod-like embodiment that connects vertebrae.

FIG. 6 shows a partially-transparent side view of the upper cylindrical segment. The segment has six non-central longitudinal channels. Alternating channels around the perimeter contain either a longitudinal spring or a longitudinal wire.

FIG. 7 shows an opaque view of the bottom end of the upper cylindrical segment in FIG. 5.

Figure 8:
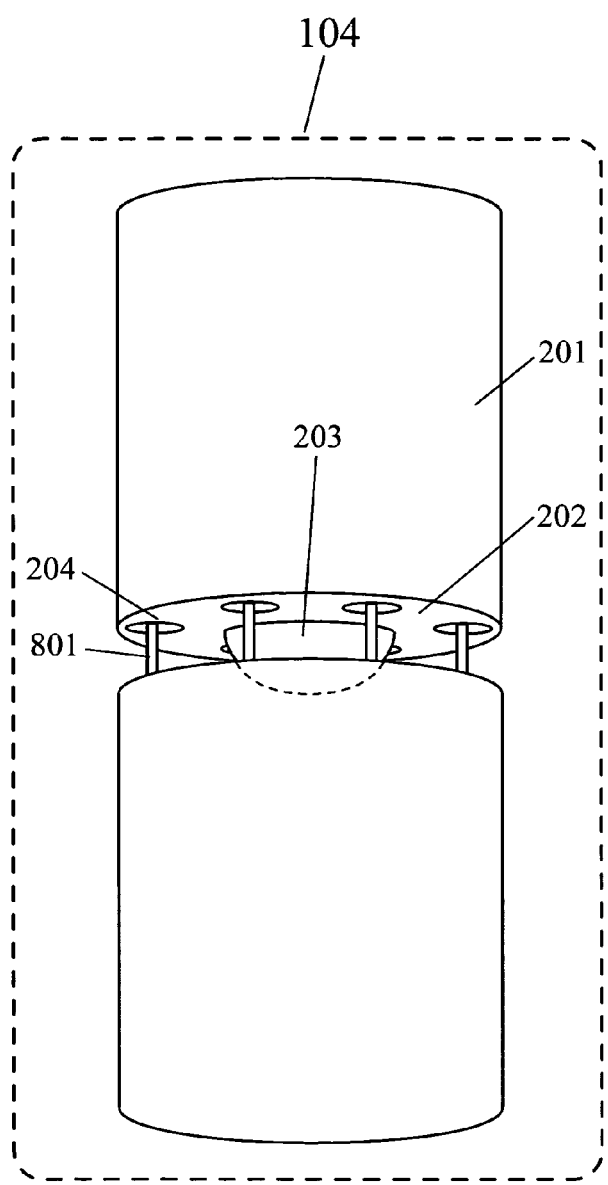

FIG. 8 shows details for a third rod-like embodiment of this device. It shows a primarily-opaque side view of two of the multiple segments that comprise the rod-like embodiment that connects vertebrae.

Figure 9:
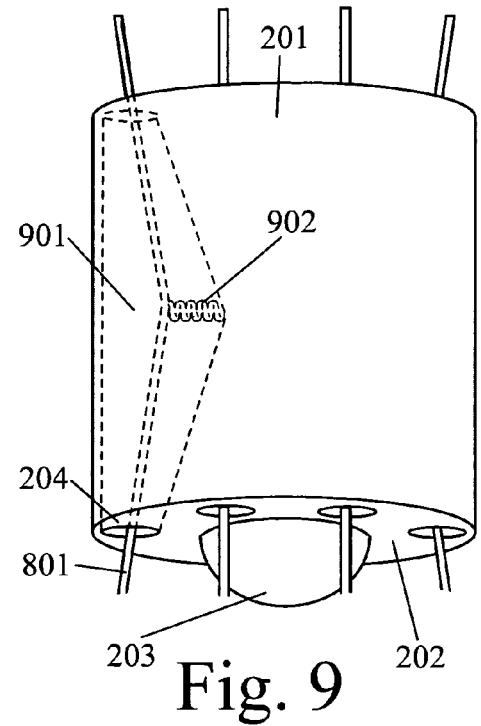

FIG. 9 shows a partially-transparent side view of the upper cylindrical segment. The segment has six non-central longitudinal channels. Each channel contains a wire with a perpendicular spring attached to it.

Figure 10:
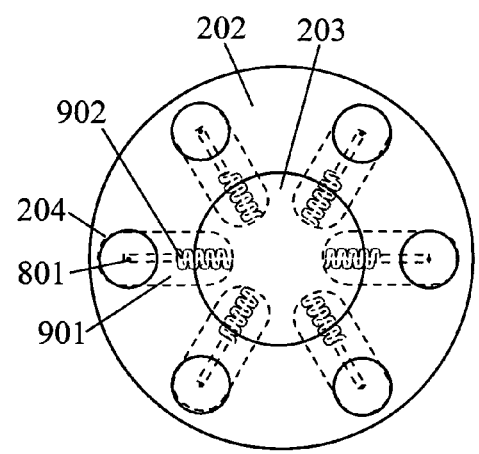

FIG. 10 shows an opaque view of the bottom end of the upper cylindrical segment in FIG. 8.

Figure 11:
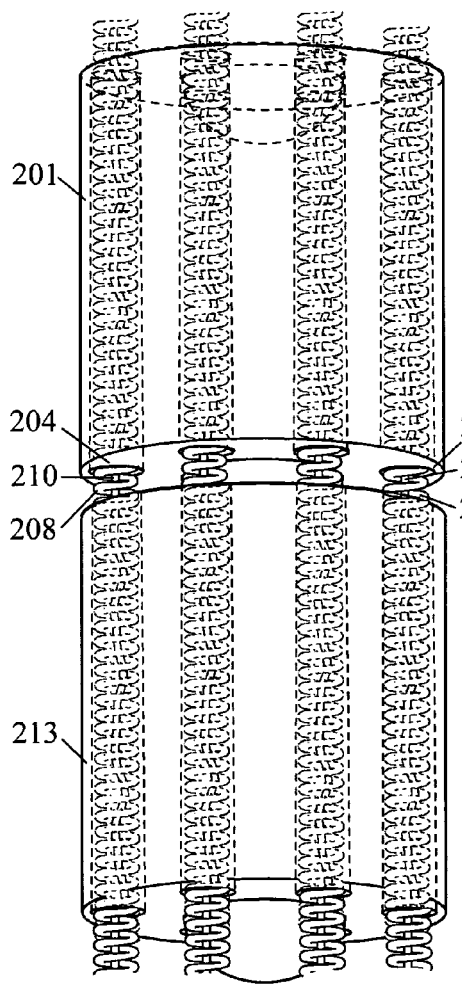
Figure 12:
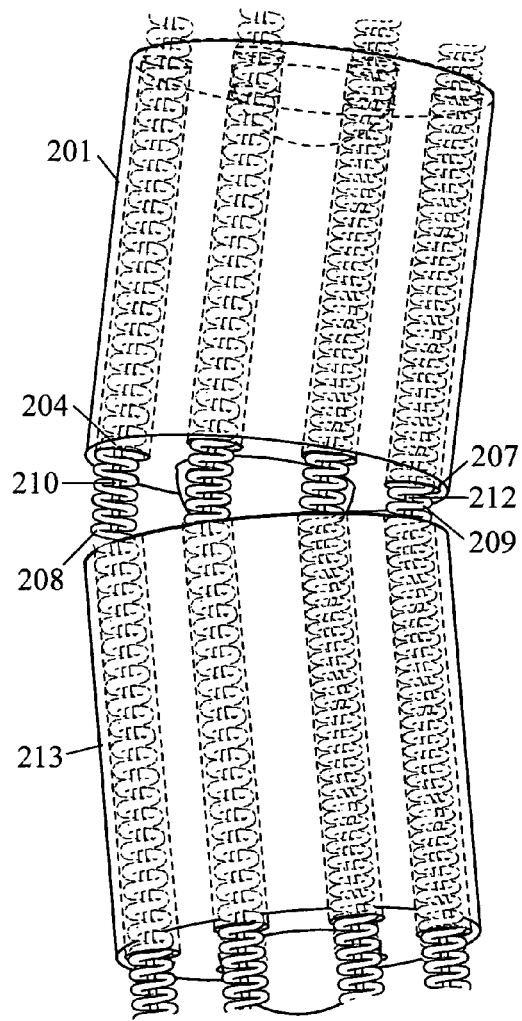

FIGS. 11 and 12 show how components in the first embodiment of the device, shown in FIGS. 2-4, move when the spine tilts.

Figure 13:
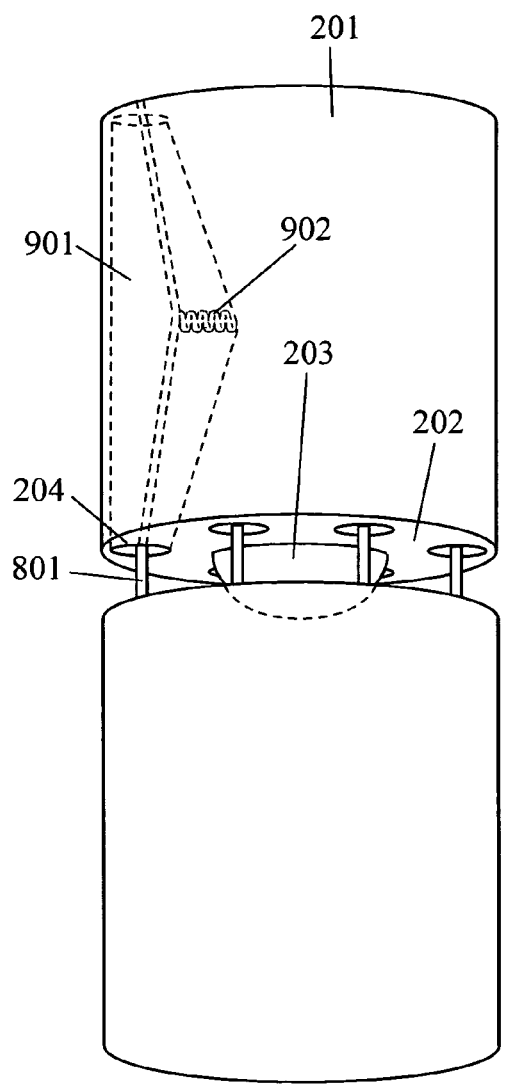
Figure 14:
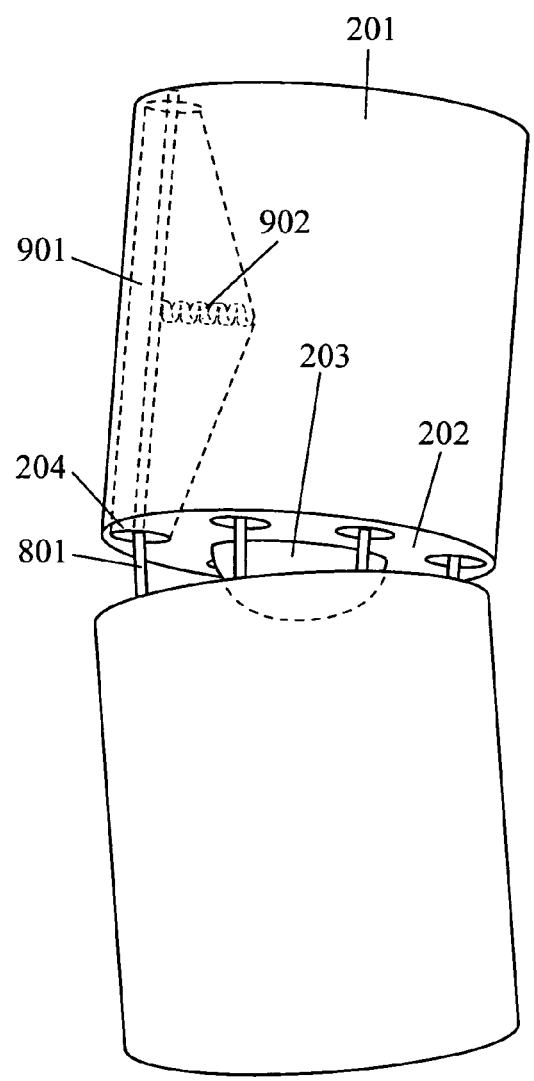

FIGS. 13 and 14 show how components in the third embodiment of the device, shown in FIGS. 8-10, move when the spine tilts.

Figure 15:
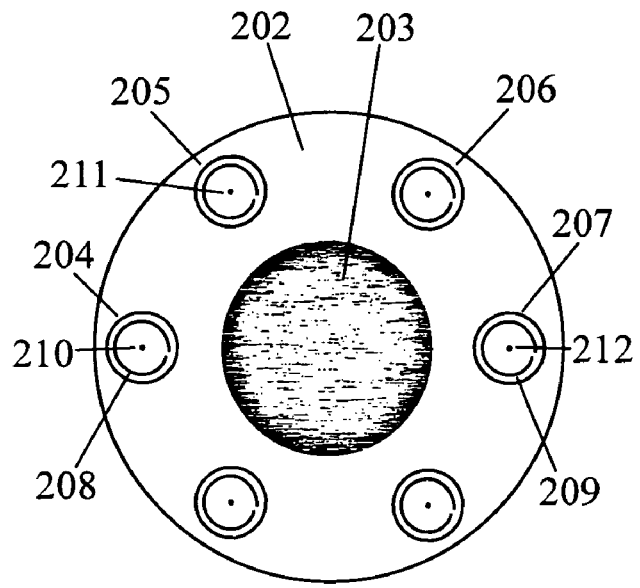
Figure 16:
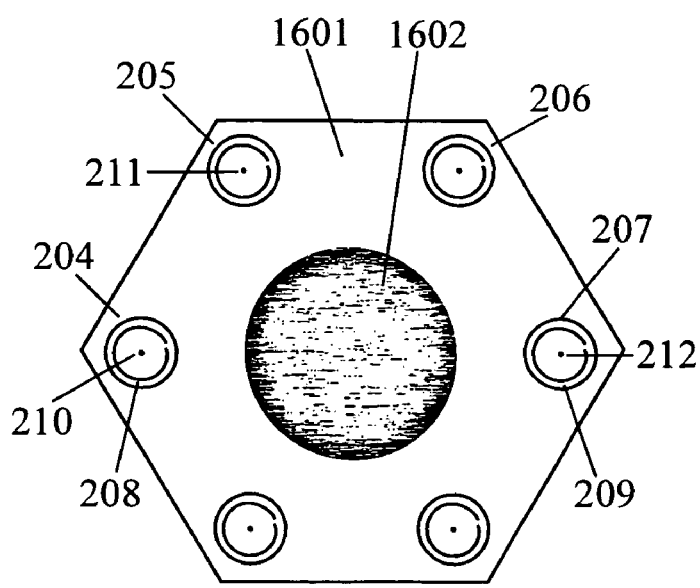

FIGS. 15 and 16 illustrate variation in the cross-sectional shape of the segments.

DETAILED DESCRIPTION OF THE FIGURES

These figures show different examples of how this invention may be embodied. However, these examples are not exhaustive. These figures do not limit the full generalizability of the claims.

Figure 1:
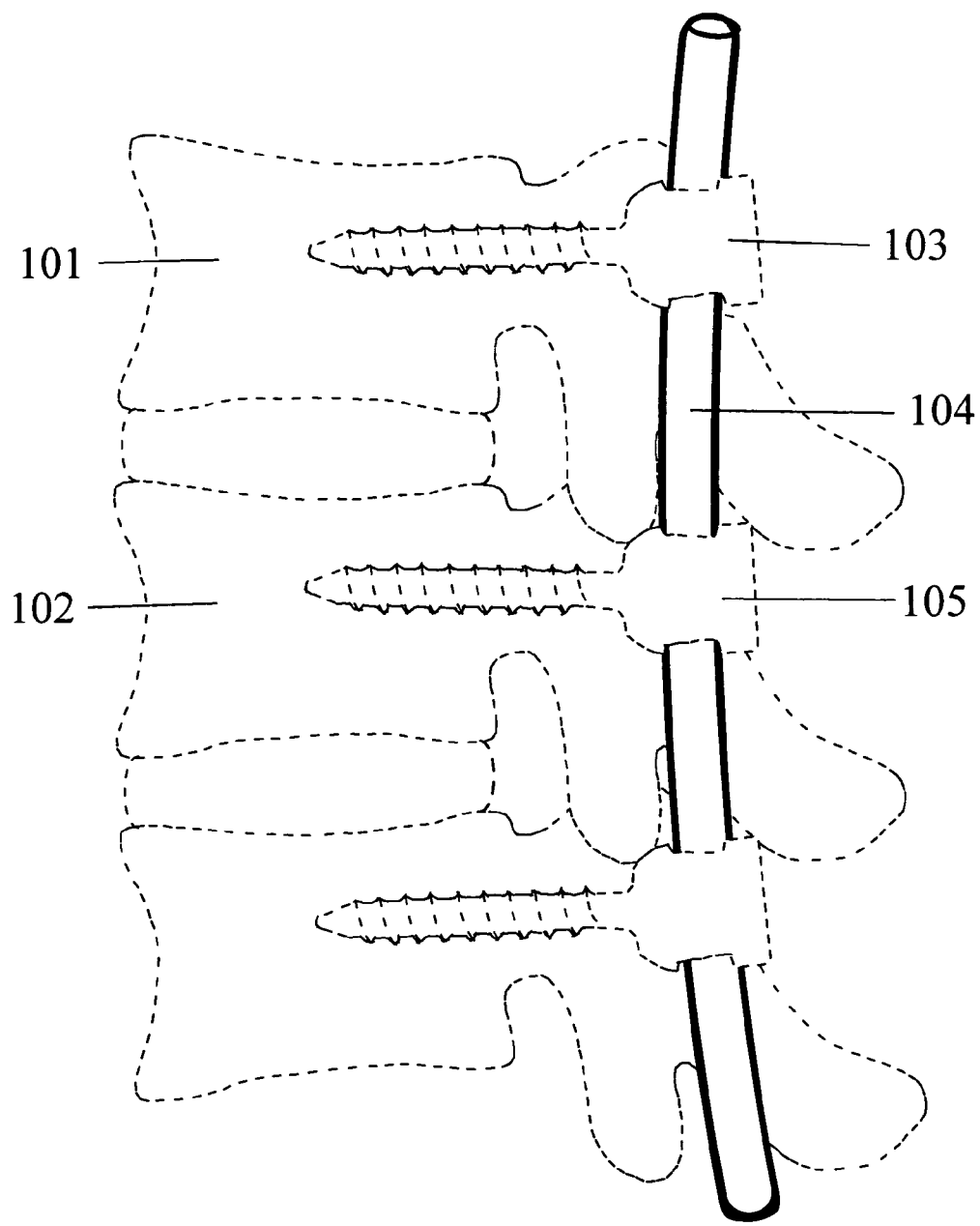
FIG. 1 shows an outline view of a rod-like embodiment of this device that has been implanted and connected to spinal vertebrae.

FIG. 1 shows an outline of a rod-like embodiment 104 of this device attached to screws (including 103 and 105) that are in turn connected to spinal vertebrae (including 101 and 102). This figure shows anatomical context for how this device may be used to connect spinal vertebrae in a manner that allows desirable movement of the spine and prevents undesirable movement of the spine. The rod-like embodiment is outside the intervertebral disk space. Different examples of design details within the rod-like outline are shown in the figures that follow.

FIG. 2 shows details for one rod-like embodiment of this device, filling in details within the rod-like outline 104 that was shown in FIG. 1. Specifically, FIG. 2 shows a primarily-opaque, side view of two of the cylindrical segments (201 and 213) that are part of a longitudinal sequence of multiple cylindrical segments forming rod-like outline 104 in FIG. 1. In FIG. 2, upper cylindrical segment 201 is shown with six channels (including 204, 205, 206, and 207) that run through the cylinder longitudinally and intersect its circular cross-section in a roughly circular manner.

Since FIG. 2 is a primarily-opaque view of the segments, the channels are only visible where they open onto bottom end portion 202 of upper cylindrical segment 201. Two of the six channels do not appear in this view because they are obscured by partial ball-like protrusion 203 that protrudes from the bottom end portion 202 of upper cylindrical segment 201. This ball-like protrusion 203 fits into a socket 214 in the top end portion of lower cylindrical segment 213. This ball-like protrusion 203 and socket 214 comprise a partial ball-and-socket joint between upper segment 201 and lower segment 213.

In this embodiment, within each of the longitudinal channels, there is a coaxial set of longitudinal members including a longitudinal spring and a longitudinal wire inside the spring. These springs and wires run longitudinally through the upper and lower segments (201 and 213) and connect these segments to each other. For example, longitudinal channel 204 contains spring 208 with wire 210 coaxially inside the spring. In this embodiment, there is a partial ball-and-socket joint between the two segments that helps to keep them aligned and that helps them to tilt smoothly as the spine moves. The partial ball portion 203 of this joint is shown protruding downward from the bottom end portion 202 of upper cylindrical segment 201. The partial ball portion 203 fits into the partial socket portion 214 which recedes into the top end portion of lower cylindrical segment 213.

FIG. 3 shows a partially-transparent side view of the upper cylindrical segment 201 that was introduced in FIG. 2. FIG. 3 shows interior transparent views of four of the six longitudinal channels, each including a longitudinal spring with a wire running longitudinally through its center. If this figure were fully transparent, then the rear two channels would also be shown. However, such full transparency would clutter the figure too much, so the rear two channels are not shown. This is why this figure is called a partially transparent, rather than a fully transparent, side view.

FIG. 3 introduces some important members that did not appear in FIG. 2 because FIG. 2 is opaque. Specifically, FIG. 3 shows fasteners 301 and 302 that attach the springs and wires to the cylindrical segments in central locations within each cylindrical segment. If the springs and wires were completely unattached and free to shift through the channels in all of the segments that they connect, then the springs and wires would not limit movement of the segments to a desirable range of motion and would not provide dynamic stabilization of the spine. In this example, the springs and wires are attached to each cylindrical segment in the center of each segment. In another example, the springs and wires could be attached only to the top of the uppermost segment in the longitudinal sequence of segments and to the bottom of the bottommost segment in the longitudinal sequence of segments.

In the embodiment of this device shown in FIGS. 2 and 3, the rigidity of the two cylindrical segments (201 and 213), connected by ball 203 and socket 214, resists longitudinal compression of the spine, but allows some degree of tilting, rotation, and longitudinal extension of the spine. The inelasticity of the connecting wires (including wires 210, 211, and 212) limits the degree of tilting, rotation, and longitudinal extension to a desirable range of motion. The force resistance of the connecting springs (including 208 and 209) dampens movement of the spine within this allowable range of motion. Acting together, these components provide dynamic stabilization of the spine. They advantageously allow dampened movement within a desired range of motion and prevent movement outside this desired range of motion.

In this example, there is some slack in all of the connecting wires when the spine is in a baseline configuration with minimal longitudinal extension, tilting, and rotation. This baseline configuration is represented by the longitudinal alignment of the two cylindrical segments shown, 201 and 213. Subsequent figures will show an example of how slack in different wires increases or decreases when the spine tilts. When slack in a wire decreases to zero from this tilting motion, then the wire becomes taut and prevents further movement in that direction. This is how the substantially-inelastic members, embodied by wires in this example, prevent undesirable movement of spinal vertebrae relative to each other.

FIG. 4 shows an opaque view of the bottom end portion 202 of upper cylindrical segment 201. This view shows openings from the six longitudinal channels (including 204, 205, 206, and 207) distributed in a roughly-circular manner around the perimeter of the circular end portion of the cylinder. This view also shows a coaxial pair of longitudinal members, including a spring and a wire inside the spring, within each channel. For example, spring 208 with wire 210 inside is located within channel 204. Finally, this view shows ball-like protrusion 203 in the center of bottom end portion 202.

In this example, the six longitudinal channels are distributed evenly, in a roughly circular pattern, near the perimeter of the cross-sectional area of cylindrical segment 201. In another example, the channels may be distributed unevenly or at different distances from the center. The exact pattern of channel distribution in the cross-sectional area is not critical, except that there must be some channels that are outside the center of the cross-section in order to provide leverage to dampen and restrict movement of the cylindrical segments relative to each other.

FIG. 5 shows details for a second embodiment of this device. It fills in details for the rod-like outline shown in FIG. 1. Specifically, FIG. 5 shows a primarily-opaque, side view of the two cylindrical segments (201 and 213) that are part of a longitudinal sequence of segments comprising the rod-like embodiment of the device shown in outline form as 104 in FIG. 1.

Similar to the first embodiment shown in FIG. 2, this second embodiment shown in FIG. 5 shows upper cylindrical segment 201 as having six longitudinal channels (including 204, 205, 206, and 207) that run through the cylinder longitudinally and intersect its circular cross-section in a roughly circular manner. However, unlike the first embodiment in FIG. 2, this second embodiment shown in FIG. 5 shows springs and wires in separate channels that alternate as one moves around the circular cross section. This is in contrast to having coaxial pairs of springs and wires in the same channel. The springs and wires run longitudinally through the upper and lower cylindrical segments (201 and 213) and connect these segments to each other. For example, longitudinal channel 204 contains spring 208 and longitudinal channel 205 contains wire 211.

Similar to the first embodiment shown in FIG. 2, the second embodiment shown in FIG. 5 shows a partial ball-and-socket joint between the two segments that helps to keep the segments aligned and allows them to tilt smoothly. The partial ball portion 203 of this joint is shown protruding downward from the lower end 202 of cylindrical segment 201. Partial ball portion 203 fits into partial socket portion 214 which recedes into the upper end of lower cylindrical segment 213.

FIG. 6 shows a partially-transparent side view of the second embodiment that was introduced in FIG. 5. FIG. 7 shows an opaque view of the bottom end portion 202 of upper cylindrical segment 201. FIG. 7 shows openings from the six longitudinal channels (including 204, 205, 206, and 207) distributed in a roughly circular manner near the perimeter of the circular end portion 202 of cylindrical segment 201. This view shows the alternating sequence of springs and wires within channels as one moves around the cross-section. For example, spring 208 is located within channel 204. Finally, FIG. 7 shows ball-like protrusion 203 in the center of end portion 202. In the embodiment shown in FIG. 7, the longitudinal channels are distributed evenly in a circular pattern and are relatively close to the exterior perimeter of cylindrical segment 201. In another example, the channels may be distributed unevenly or at different distances from the center.

FIG. 8 shows details for a third embodiment of this device, filling in details within the rod-like outline shown in FIG. 1. Specifically, FIG. 8 shows a primarily-opaque side view of two cylindrical segments (201 and 213) that are part of a longitudinal sequence of segments comprising the rod-like embodiment of the device shown in outline form as 104 in FIG. 1.

FIG. 8 shows upper cylindrical segment 201 with six channels (including 204) that run through the cylinder longitudinally and intersect its circular cross-section in a roughly circular manner. Unlike the prior two embodiments, this third embodiment has springs attached perpendicularly to wires. This is in contrast to the coaxial springs and wires in the first embodiment and the alternating springs and wires in separate channels in the second embodiment. The wires run longitudinally through the upper and lower cylindrical segments (201 and 213) and connect the segments to each other. A perpendicularly-attached spring for each wire allows dampened extension of the wire, up to the point where there is no remaining slack in the wire. This allows dampened movement within the range of desirable movement and prevents movement outside this range.

FIG. 9 shows upper cylindrical segment 201 with a transparent view of only one channel (901) to avoid cluttering the diagram with transparent views of all six channels. In FIG. 9, wire 801 has some slack, but this slack is kept in moderate tension by perpendicularly-attached spring 902.

FIG. 10 shows a partially-transparent view of the bottom end portion 202 of upper cylindrical segment 201. This view shows all six longitudinal channels (including 204, 205, 206, and 207) distributed in a roughly circular manner around the circular cross-section of the cylinder. The transparent aspect of this view shows the interior portions of these six longitudinal channels in addition to their openings onto the bottom end of the segment. In this embodiment, each of the six channels contains a wire held in moderate tension by a perpendicularly-attached spring within the cylindrical segment. This embodiment may have advantages over the prior two embodiments for some applications. For example, since the wires are kept in moderate tension at all times, there may be less chance of the wires getting tangled when they are slack.

FIGS. 11 and 12 provide partially-transparent side views of the first embodiment introduced in FIGS. 2-4 showing how the components move when cylindrical segments 201 and 213 are tilted relative to each other. In FIG. 11, cylindrical segments 201 and 213 are aligned, corresponding to the spinal column being in a configuration of minimal tilting. The spine need not be perfectly straight when the cylinders are perfectly aligned because the screws connecting the rod-like sequence of segments to the spine may have different lengths or angles along the length of the rod. Nonetheless, alignment of cylindrical segments 201 and 213 will tend to be associated with a spinal configuration of minimal tilting. Thus, alignment is thus a reasonable baseline configuration for a figure showing the effect of tilting. It should be noted that there is slack in the wires within the springs in FIG. 11. This slack allows desirable movement within a healthy range of motion.

In FIG. 12, cylindrical segments 201 and 213 have been tilted relative to each other by movement of the spine. In this example, wires on the left side of the segments (including wire 210) have been pulled taut by the tilting movement while wires on the right side of the segments (including wire 212) have become more slack. At some point, the tautness of the wires on the left side prevents further tilting of the segments in this direction. This is how the substantially-inelastic longitudinal members connecting the segments, wires in this example, prevent undesirable motion of the vertebrae relative to each other.

The tilting of segments 201 and 213 in FIG. 12 does not affect only the degree of slack in different wires. This tilting also affects the extension of different springs. For example, left-ward tilting in this example causes springs on the left side of the segments (including spring 208) to become more extended and the springs on the right side of the segments (including spring 209) to become more compressed. This is how the motion-dampening longitudinal members, springs in this example, provide advantageous dampening of vertebral motion within the range of motion allowed by the substantially-inelastic members.

FIGS. 13 and 14 provide partially-transparent side views of the third embodiment introduced in FIGS. 8-10 showing how the components move when cylindrical segments 201 and 213 are tilted relative to each other. In FIG. 13, cylindrical segments 201 and 213 are aligned. In FIG. 12, cylindrical segments 201 and 213 are tilted relative to each other by movement of the spine. As a result of this tilting, wires on the left side of the segments (including wire 801 shown in transparent view) are pulled taut and springs on the left side of the segments (including spring 902) are extended. At some point, the tautness of wires on the left side prevents further tilting of the segments in this direction. This is how the substantially-inelastic longitudinal members connecting the segments, wires in this example, prevent undesirable motion of the vertebrae relative to each other.

FIGS. 15 and 16 provide an example of variation in the cross-sectional shape of the segments comprising the sequence of longitudinal segments forming the rod-like embodiment in FIG. 1. FIG. 15 shows a segment with a circular cross-sectional shape. FIG. 15 is a repeat of FIG. 2 in order for ease of comparison on the same page with FIG. 16. FIG. 16 shows another example wherein the cross-sectional shape of the segments is a hexagon. In another example, the cross-sectional shape of the segments may be another type of polygon. In another example, the cross-sectional shape of the segments may be a non-circular and non-polygonal convex shape.

I claim:

1. An implantable device that allows desirable movement of spinal vertebrae relative to each other and prevents undesirable movement of spinal vertebrae relative to each other, comprising:
   a sequence of two or more substantially-incompressible segments wherein: this sequence is configured to connect two or more spinal vertebrae, this sequence limits longitudinal compression of spinal vertebrae, and the segments in this sequence have channels in them, wherein these channels extend through both ends of these segments, in which there are longitudinal members that connect the segments and at least one of these channels does not go through some cross-sectional centers of the segments;
   a plurality of flexible but substantially-inelastic members running through the channels in the incompressible segments, wherein these substantially-inelastic members extend through both ends of these segments, wherein decreases or increases in the slack of one or more of these inelastic members, as the spine moves, allow desirable movement of spinal vertebrae relative to each other and prevent undesirable movement of spinal vertebrae relative to each other; and
   a plurality of extendable but motion-dampening members running through the channels in the incompressible segments, wherein these motion-dampening members extend through both ends of these segments, wherein changes in the extension of one or more of these motion-dampening members dampen movement of spinal vertebrae relative to each other.

2. The device in claim 1 wherein the substantially-incompressible segments are longitudinal and connected to each other.

3. The device in claim 1 wherein the substantially-inelastic members are longitudinal and are selected from among the group consisting of: wires, cables, and inelastic cords.

4. The device in claim 1 wherein the motion-dampening members are selected from among the group consisting of: springs, rods with helical cuts, and elastic cords.

5. The device in claim 1 wherein there is slack in at least some of the substantially-inelastic members when the spine is in a baseline configuration with minimal extension, tilting, and rotation.

6. The implantable device in claim 1 wherein the relationship between the substantially-inelastic members and the motion-dampening members is selected from among the group of relationships consisting of: substantially parallel and coaxial; substantially parallel and separate; substantially parallel and connected to each other in two places; and substantially perpendicular and connected to each other in one place.

7. The implantable device in claim 1 wherein the cross-sectional shape of the substantially-incompressible segments is selected from among the group of: circular, oval, hexagonal, octagonal, or other convex shape.

8. The implantable device in claim 1 wherein the shape of the ends of the substantially-incompressible segments is flat, rounded, or curved.

9. The implantable device in claim 1 wherein there is an additional central flexible layer or a rotating joint member between the substantially-incompressible segments to guide movement between substantially-incompressible segments.

10. The implantable device in claim 1 wherein the slack of the substantially-inelastic members can be adjusted before, during, or after implantation to change the motion allowed by the device for therapeutic effect.

11. The adjustment of slack in claim 10 wherein this adjustment is performed: manually by direct physical contact with the device; manually by remote communication with an actuator; or automatically based on interaction between sensors and actuators.

12. An implantable device that allows desirable movement of spinal vertebrae relative to each other and prevents undesirable movement of spinal vertebrae relative to each other, comprising:
 a longitudinal sequence of two or more connected and substantially-incompressible segments wherein: this sequence is configured to connect two or more spinal vertebrae, this sequence limits longitudinal compression of spinal vertebrae, and the segments in this sequence have channels in them from the top of the uppermost segment to the bottom of the bottommost segment in which there are longitudinal members that connect the segments and at least two of which do not go through some cross-sectional centers of the segments;
 a plurality of longitudinal and flexible but substantially-inelastic members running through the channels in the incompressible segments from the top of the uppermost segment to the bottom of the bottommost segment: wherein these inelastic members connect the incompressible segments; wherein decreases or increases in the slack of one or more of these inelastic members, as the spine moves, allow desirable movement of spinal vertebrae relative to each other and prevent undesirable movement of spinal vertebrae relative to each other; wherein there is slack in at least some of these inelastic members when the spine is in a baseline configuration with minimal extension, tilting, and rotation; and
 a plurality of longitudinal and extendable but motion-dampening members running through the channels in the incompressible segments from the top of the uppermost segment to the bottom of the bottommost segment, wherein changes in the extension of one or more of these motion-dampening members as the spine moves dampen movement of spinal vertebrae relative to each other.

13. The implantable device in claim 12 wherein the relationship between the substantially-inelastic members and the motion-dampening members is selected from among the group of relationships consisting of: substantially parallel and coaxial; substantially parallel and separate; substantially parallel and connected to each other in two places; and substantially perpendicular and connected to each other in one place.

14. The implantable device in claim 12 wherein the cross-sectional shape of the substantially-incompressible segments is selected from among the group of: circular, oval, hexagonal, octagonal, or other convex shape.

15. The implantable device in claim 12 wherein the shape of the ends of the substantially-incompressible segments is flat, rounded, or curved.

16. The implantable device in claim 12 wherein there is an additional central flexible layer or a rotating joint member between the substantially-incompressible segments to guide movement between substantially-incompressible segments.

17. The implantable device in claim 12 wherein the slack of the substantially-inelastic members can be adjusted before, during, or after implantation to change the motion allowed by the device for therapeutic effect.

18. The adjustment of slack in claim 17 wherein this adjustment is performed: manually by direct physical contact with the device; manually by remote communication with an actuator, or automatically based on interaction between sensors and actuators.

* * * * *